United States Patent
Lisanti et al.

(10) Patent No.: US 11,561,227 B2
(45) Date of Patent: Jan. 24, 2023

(54) ANTI-MITOCHONDRIAL INHIBITORS FOR ONCOGENIC RAS AND MYC

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 418 days.

(21) Appl. No.: 16/753,493

(22) PCT Filed: Oct. 11, 2018

(86) PCT No.: PCT/US2018/055451
§ 371 (c)(1),
(2) Date: Apr. 3, 2020

(87) PCT Pub. No.: WO2019/075226
PCT Pub. Date: Apr. 18, 2019

(65) Prior Publication Data
US 2020/0292551 A1 Sep. 17, 2020

Related U.S. Application Data

(60) Provisional application No. 62/570,970, filed on Oct. 11, 2017.

(51) Int. Cl.
G01N 33/53 (2006.01)
G01N 33/574 (2006.01)
A61K 31/138 (2006.01)
G01N 33/50 (2006.01)
G01N 33/543 (2006.01)
G01N 33/569 (2006.01)

(52) U.S. Cl.
CPC ..... *G01N 33/57496* (2013.01); *A61K 31/138* (2013.01); *G01N 33/5005* (2013.01); *G01N 33/5073* (2013.01); *G01N 33/54326* (2013.01); *G01N 33/56966* (2013.01); *G01N 33/57415* (2013.01); *G01N 33/57492* (2013.01)

(58) Field of Classification Search
CPC .................................................. G01N 33/53
USPC ......................................................... 436/526
See application file for complete search history.

(56) References Cited

U.S. PATENT DOCUMENTS

| 2001/0002404 A1 | 5/2001 | Webb |
| 2006/0019256 A1 | 1/2006 | Clarke et al. |
| 2016/0339106 A1 | 11/2016 | Dhar |
| 2017/0014361 A1 | 1/2017 | Dhar |

FOREIGN PATENT DOCUMENTS

| CA | 2 754 610 | 9/2010 |
| WO | 2005/005601 A2 | 1/2005 |
| WO | 2006/135886 A2 | 12/2006 |
| WO | 2018/170109 | 9/2018 |
| WO | 2018/213751 | 11/2018 |
| WO | 2019/005698 | 1/2019 |
| WO | WO 2019104115 | 5/2019 |
| WO | WO 2019126179 | 6/2019 |

OTHER PUBLICATIONS

Lee, Kyung-Min et al., "MYC and MCL1 Cooperatively Promote Chemotherapy-Resistant Breast Cancer Stem Cells via Regulation of Mitochondrial Oxidative Phosphorylation", Cell Metabolism, vol. 26, No. 4, Oct. 3, 2017, p. 633, XP085239425.
Federica Sotgia et al: "Mitochondrial markers predict recurrence, metastasis and tamoxifen-resistance in breast cancer patients: Early detection of treatment failure with companion diagnostics", Oncotarget, vol. 8, No. 40, Sep. 15, 2017 (Sep. 15, 2017), pp. 68730-68745, XP055659674.
Rebecca Lamb et al: "Mitochondria as new therapeutic targets for eradicating cancer stem cells: Quantitative proteomics and functional validation via MCT1/2 inhibition", Oncotarget vol. 5, No. 22, Nov. 30, 2014 (Nov. 30, 2014), XP055482861.
Rebecca Lamb et al: "Antibiotics that target mitochondria effectively eradicate cancer stem cells, across multiple tumor types: Treating cancer like an infectious disease", Oncotarget, vol. 6, No. 7, Mar. 10, 2015 (Mar. 10, 2015), pp. 4569-4584, XP055405961.
Dobbin Zachary C. et al: "Isolation and Characterization of Potential Cancer Stem Cells from Solid Human Tumors-Potential Applications", Current Protocols in Pharmacology, vol. 63, No. 1, Dec. 1, 2013 (Dec. 1, 2013), XP055794465.
Fionnuala Morrish, et al., "MYC and Mitochondiral Biogenesis", Cold Springs Harbor Perspectives in Medicine, May 1, 2014, vol. 4, No. 5, 7 pages.
International Search Report for PCT/US2018/055451 dated Jan. 9, 2019, 2 pages.
Written Opinion of the ISA for PCT/US2018/055451 dated Jan. 9, 2019, 6 pages.

*Primary Examiner* — Sean E Aeder
(74) *Attorney, Agent, or Firm* — Nixon & Vanderhye, P.C.

(57) ABSTRACT

The present disclosure relates to a Proteomics-to-Genomics approach allows for in silico validation of biomarkers and drug targets. Biomarkers having high prognostic value in predicting cancer patient populations that may benefit from mitochondrial biogenesis inhibitor therapy may be identified under the present approach. Also disclosed are methods for identifying candidates for anti-mitochondrial therapy, and in particular mitochondrial biogenesis inhibitor therapy. Diagnostic kits including reagents for determining transcripts or probes of high prognostic value are also disclosed. Additionally, mitochondrial biogenesis inhibitors may be used as anti-cancer agents for diverse oncogenic stimuli, including for example, c-MYC and H-Ras oncogenes, as well as environmental stimuli such as, for example rotenone.

10 Claims, 19 Drawing Sheets

N=152

N=149

ANTI-MITOCHONDRIAL INHIBITORS FOR ONCOGENIC RAS AND MYC

This application is the U.S. national phase of International Application No. PCT/US2018/055451 filed Oct. 11, 2018 which designated the U.S. and claims priority to U.S. Provisional Patent Application No. 62/570,970 filed Oct. 11, 2017, the entire contents of each of which are hereby incorporated by reference.

FIELD

The present disclosure relates to methods of identifying candidates for anti-mitochondrial inhibitor therapy. The present disclosure also relates to diagnostic kits including reagents for determining transcripts or probes of high prognostic value for anti-mitochondrial inhibitor therapy.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

c-Myc and H-Ras genes have been identified as proto-oncogenes that can be dysregulated by genetic amplification and/or specific activating mutations. Vogt, *Nat Rev Cancer* 2012; 12(9):639-648. c-Myc and H-Ras have also been shown to cooperate in promoting cell transformation and tumorigenesis. Wang et al, *Cell Cycle* 2011; 10(1):57-67. However, the mechanism by which c-Myc and H-Ras cooperate to promote or facilitate oncogenic transformation remains unknown.

SUMMARY

Disclosed herein are anti-mitochondrial inhibitor therapies, and in particular mitochondrial biogenesis inhibitors, that may be used as anti-cancer agents for diverse oncogenic stimuli, including for example, c-MYC and H-Ras oncogenes, as well as environmental stimuli such as, for example rotenone. It is an object of this disclosure to demonstrate that c-Myc and H-Ras act synergistically to increase the capacity of cancer cells to undergo anchorage-independent growth and to amplify their energetic activity, increasing both mitochondrial respiration (c-Myc) and the glycolytic pathway (H-Ras). It is also an object of this disclosure to demonstrate that treatment of the cancer cells with doxycycline, an inhibitor of mitochondrial biogenesis, is sufficient to halt and/or prevent increases in cancer stem cell (CSC) propagation driven by c-Myc and H-Ras, and by rotenone, a known mitochondrial poison. This demonstrates that mitochondrial biogenesis is required to stimulate CSC propagation. Mitochondrial biogenesis inhibitors, such as doxycycline, mitoriboscins (mitoribosome-targeted therapeutics having anti-cancer and antibiotic properties), mitoketoscins (non-carcinogenic compounds that bind to at least one of ACAT1/2 and OXCT1/2 and inhibit mitochondrial ATP production), and antimitoscins (antibiotics having intrinsic anti-mitochondrial properties that are chemically modified to target the antibiotics to mitochondria), therefore represent a new classes of therapeutics that target CSC mitochondrial biogenesis, and importantly provide for a novel and "mutation-independent" approach to cancer therapy. International Patent Application PCT/US2018/022403, filed Mar. 14, 2018, is incorporated by reference in its entirety. International Patent Application PCT/US2018/033466, filed May 18, 2018, is incorporated by reference in its entirety. International Patent Application PCT/US2018/039354, filed Sep. 26, 2018, is incorporated by reference in its entirety. Further, it is an object of this disclosure to show that inhibition of mitochondrial biogenesis, an anti-mitochondrial inhibitor therapy, represents a new phenotype-based strategy for mutation-independent anti-cancer therapy. The Proteomics-to-Genomics approach described herein allows for in silico validation of biomarkers and drug targets. For example, under the present approach, we invented a Myc-based biomarker, generally referred to as a Mito-Signature™, that includes 3 mitochondrial genes (HSPD1; COX5B; TIMM44) for effectively predicting tumor recurrence (HR=4.69; p=2.4e-08) and distant metastasis (HR=4.94; p=2.8e-07), in ER(+) in breast cancer patients. This gene signature could serve as a new companion diagnostic for the early prediction of treatment failure in patients receiving hormonal therapy.

The present approach may take the form of a method of detecting cancer stem cells in a tissue sample. In some embodiments, methods may include identifying a Myc-based biomarker, identifying a fluorescent antibody directed against the Myc-based biomarker, administering the identified fluorescent antibody to the sample; sorting cells from the sample; and detecting the fluorescent antibody in the sorted cells. A Myc-based biomarker may include one or more of HSPD1, COX5B, and/or TIMM44. For example, the Myc-based biomarker may include HSPD1, COX5B, and TIMM44.

Some embodiments of the present approach may take the form of methods for isolating cancer stem cells in a tissue sample. Such methods may include, for example, identifying a Myc-based biomarker, identifying a fluorescent antibody directed against the Myc-based biomarker, administering the identified fluorescent antibody to the sample, sorting cells from the sample, and separating cells based on the presence of the fluorescent antibody.

Some embodiments may take the form of a method of detecting cancer stem cells in a tissue sample. Such methods may include, for example, identifying a Myc-based biomarker, identifying an antibody directed against the Myc-based biomarker, coupling the antibody with a magnetic element, administering the coupled antibody to the sample, sorting cells from the sample, and detecting the presence of the magnetic element in the sorted cells. Magnetic elements can be, for example, magnetic beads.

Embodiments of the present approach may take the form of methods for isolating cancer stem cells in a tissue sample. Methods may include, for example, identifying a Myc-based biomarker, identifying an antibody directed against the Myc-based biomarker, coupling the antibody with a magnetic element (such as magnetic beads), administering the coupled antibody to the sample, sorting cells from the sample, and detecting the presence of the magnetic element in the sorted cells.

The present approach may employ what the inventors have labeled a Proteomics-to-Genomics methodology. In some embodiments the present approach may take the form of a method for identifying candidates for an anti-mitochondrial inhibitor therapy, and in particular mitochondrial biogenesis inhibitor therapy. These embodiments may involve determining the level of at least one of a transcript and a probe with high prognostic value, such as in a sample from a patient. The sample may be, for example, tissue (such as for example, a tumor tissue sample), whole blood, plasma, serum, urine, cerebrospinal fluid, saliva, etc. Next, the sample (or, e.g., the patient) may be classified as a candidate for mitochondrial biogenesis inhibitor therapy if the sample has an increased level, relative to a threshold level, of the transcript and/or probe with high prognostic value. Candidates may be administered an mitochondrial biogenesis inhibitor, such as, for example, known inhibitors, a mitoriboscin, a mitoketoscin, and/or an anti-mitoscin. In some embodiments, the transcript and/or probe with high prognostic value comprises at least one of HSPD1, COX5B, and TIMM44, and in some embodiments includes HSPD1, COX5B, and TIMM44. In some embodiments, the transcript and/or probe with high prognostic value comprises at least one of a protein product and a peptide.

Some embodiments of the present approach may take the form of a diagnostic kit for identifying a patient with a disease or disorder to receive an anti-mitochondrial inhibitor therapy, such as a mitochondrial biogenesis inhibitor. The kit may include at least one reagent for determining the level of one or more transcripts and/or probes with high prognostic value in a sample. The disease may be a cancer, such as, for example, circulating cancer cells, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies.

In some embodiments, the present approach may be in the form of a method of identifying a biomarker. In some embodiments, the method may include isolating at least one protein from a tumor sample. The levels of mRNA transcripts corresponding to the protein(s) may be determined through, for example, proteomics. mRNA transcripts having levels in excess of normal levels (e.g., accepted levels, levels from healthy tissue, published levels, etc.) may be identified as having prognostic value. Those mRNA transcripts may then be used as biomarkers for the original tumor.

The present approach may also take the form of a method for identifying biomarkers beginning with a cell line. In such embodiments, the cell line may be altered with a genetic change, an epigenetic change, and/or a metabolic change, then proteins may be isolated from the altered cell line. Levels of mRNA transcripts corresponding to the isolated protein(s) may be determined. Next, mRNA transcript(s) may be classified as having prognostic value if the mRNA transcript level is changed relative to a normal level for the mRNA transcript. It should be appreciated that normal levels may be determined through various methods, such as by comparison to unaltered cell lines and using published data, among other approaches as may be known in the art. The mRNA transcripts having prognostic value may then be used as a biomarker for the alteration. Also, the present approach may generate a prognostic signature having at least one mRNA transcript with a prognostic value. Embodiments may further include validation of the prognostic signature. The validation may include, for example, comparing the levels of mRNA transcripts in tumor or altered cells with published levels for the mRNA transcripts in normal cells.

In embodiments of the present approach, isolated protein may be associated with at least one or mitochondria, glycolysis, fatty acid oxidation, and pentose phosphate pathway. In embodiments of the present approach, the normal mRNA transcript levels nay be determined from non-tumor cell samples, unaltered cell lines, and other published data. The present approach may also take the form of biomarkers. For example, a biomarker described herein may include at least one of HSPD1, COX5B, and TIMM44, and in some embodiments it may include HSPD1, COX5B, and TIMM44. The present approach may also be used to identify Mito-Signatures—gene signatures having one or more biomarkers with a high (i.e., statistically significant, P-value <0.05) hazard ration value—that serve as companion diagnostics for the early prediction of treatment failure in patients receiving hormonal therapy.

DESCRIPTION

The following description illustrates embodiments of the present approach in sufficient detail to enable practice of the present approach. Although the present approach is described with reference to these specific embodiments, it should be appreciated that the present approach may be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

Mitochondrial metabolism is an untapped gateway for treating a number of afflictions, ranging from cancer to bacterial and fungal infections to aging. Functional mitochondria are required for the propagation of cancer stem cells. Inhibiting mitochondrial metabolism in cancer cells impedes the propagation of those cells. The present approach explored this gateway through CSC propagation driven by c-Myc and H-Ras.

c-Myc and H-Ras have been shown to be proto-oncogenes that promote cell transformation and tumorigenesis. However, the mechanism by which this occurs is unknown. c-Myc and/or H-Ras transcripts that are implicated in cancer cell transformation and tumorigenesis may be identified through a convergent approach of in vitro and in vivo validation of tumorigenesis and metabolic phenotyping.

Investigation of the mechanism of tumorigenesis may be conducted by transduction of MCF7 cells with c-Myc, H-Ras, or both, and then subjecting the cell lines to phenotypic characterization, such as mammosphere formation. For the mammosphere formation assay inventors employed, a single suspension of MCF7 cells was prepared using enzymatic (lx Trypsin-EDTA, Sigma Aldrich) and manual disaggregation with a 25-gauge needle. Cells were plated at a density of 500 cells/cm$^2$ in a mammosphere medium (DMEM-F12/B27/20-ng/mlEGF/PenStrep) in non-adherent conditions, in culture dishes coated with 2-hydroxyethyl-methacrylate (poly-HEMA, Sigma). Cells were grown for 5 days and maintained in a humidified incubator at 37° C. at an atmospheric pressure in 5% (v/v) carbon dioxide/air. After 5 days in culture, spheres >50 μm were counted using an eye-piece graticule, and the percentage of cells plated which formed spheres was calculated and is referred to as percent mammosphere formation, normalized to vehicle-alone treated controls. Mammosphere assays were performed in triplicate and repeated three times independently.

Figure 1:
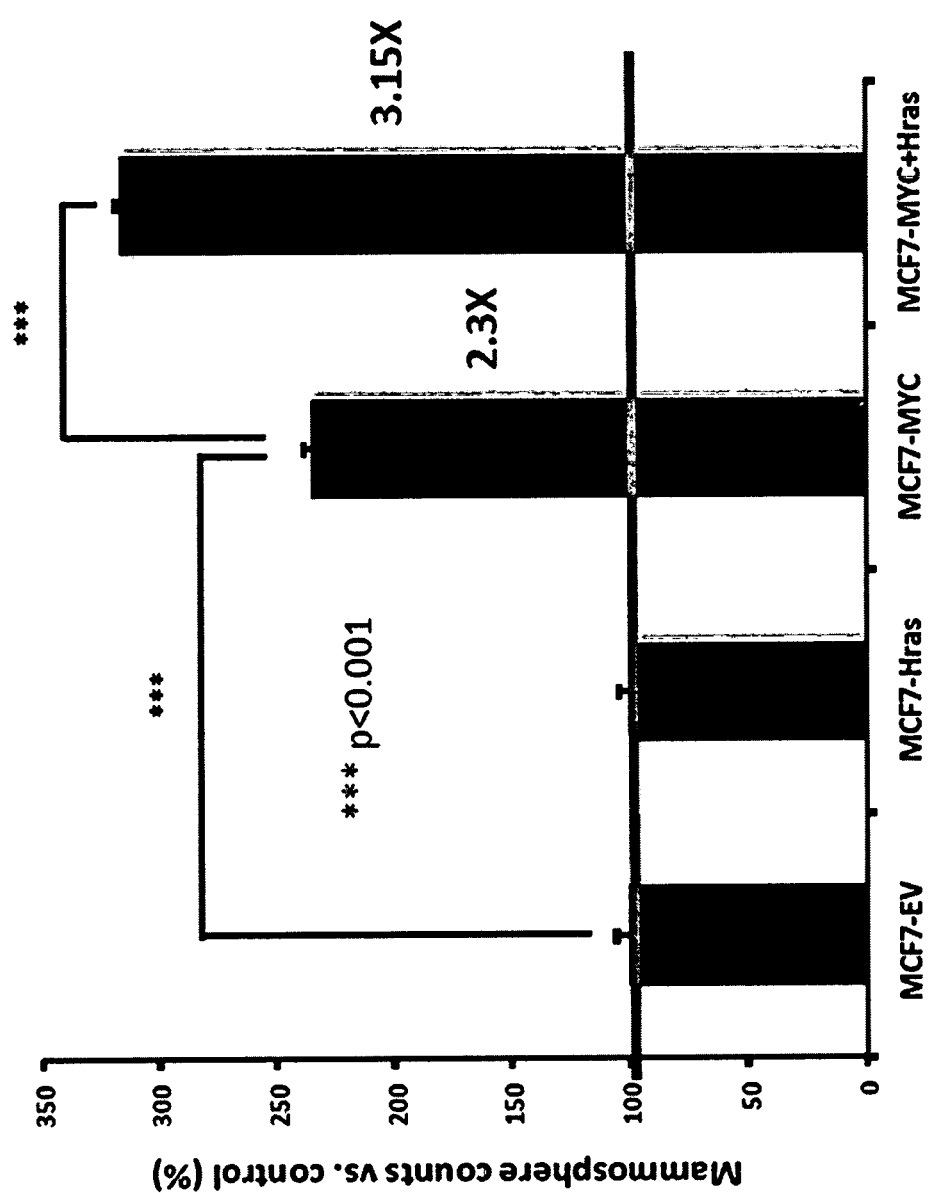
FIG. 1 shows the effects of H-Ras, c-Myc, and H-Ras plus c-Myc on mammosphere formation in MCF7 cells.

FIG. 1 shows the effects of H-Ras, c-Myc, and H-Ras plus c-Myc on mammosphere formation in MCF7 cells. Mammosphere formation is generally regarded as a measure of CSC activity and/or anchorage-independent growth. H-Ras alone had no effect on mammosphere formation, whereas c-Myc increased mammosphere formation by about 2.3-fold. Co-expression of both c-Myc and H-Ras appeared to synergistically increase mammosphere formation by 3.15-fold. It should be appreciated that those skilled in the art may transduce and assess mammosphere formation in other cancer types, as CSCs show conserved or similar features across most cancer types.

To understand how c-Myc and H-Ras cooperate to fuel CSC propagation, the MCF7 cells may be subjected to metabolic phenotyping using a Seahorse XFe96 metabolic flux analyzer. It should be appreciated that those skilled in the art may investigate metabolic phenotyping by other methods known in the art. For the metabolic assay inventors employed, MCF7 cells were maintained in DMEM supplemented with 10% FBS (fetal bovine serum), 2 mM GlutaMAX, and 1% Pen-Strep. 8,000 cells per well were seeded into XF96-well cell culture plates, and incubated overnight at 37° C. in a 5% CO2 humidified atmosphere. The next day, cells were washed in pre-warmed XF assay media (for OCR measurement, XF assay media was supplemented with 10 mM glucose, 1 mM Pyruvate and adjusted at pH 7.4). Cells were then maintained in 175 μL/well of XF assay media at 37° C., in a non-$CO_2$ incubator for 1 h. During incubation, 25 μL of 80 mM glucose, 9 μM oligomycin, 1M 2-deoxy-glucose (for ECAR measurement) and 25 μL of 10 μM oligomycin, 9 μM FCCP, 10 μM rotenone, 10 μM antimycin A (for OCR measurement) in XF assay media was loaded into the injection ports of the XFe-96 sensor cartridge. During the experiment, the instrument injected these inhibitors into the wells at a given time point, while ECAR/OCR was measured continuously. ECAR and OCR measurements were normalized by protein content (using a Sulphorhodamine B assay). Data sets were analyzed by XFe-96 software, using one-way ANOVA and Student's t-test calculations. All experiments were performed in triplicate.

Figure 2A:
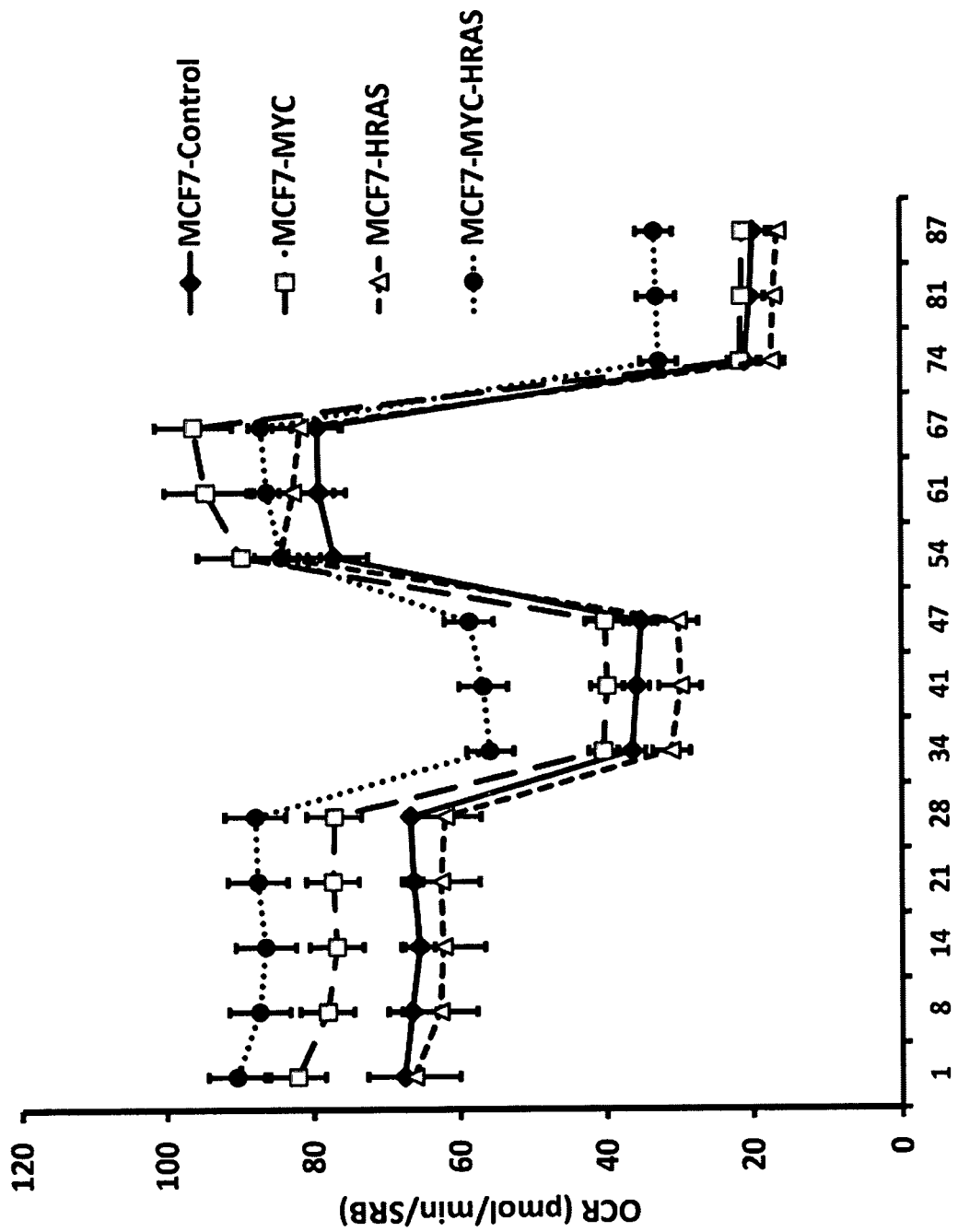
FIG. 2A shows the effects of H-Ras, c-Myc, and H-Ras plus c-Myc on oxygen consumption rate (OCR).
Figure 2B:
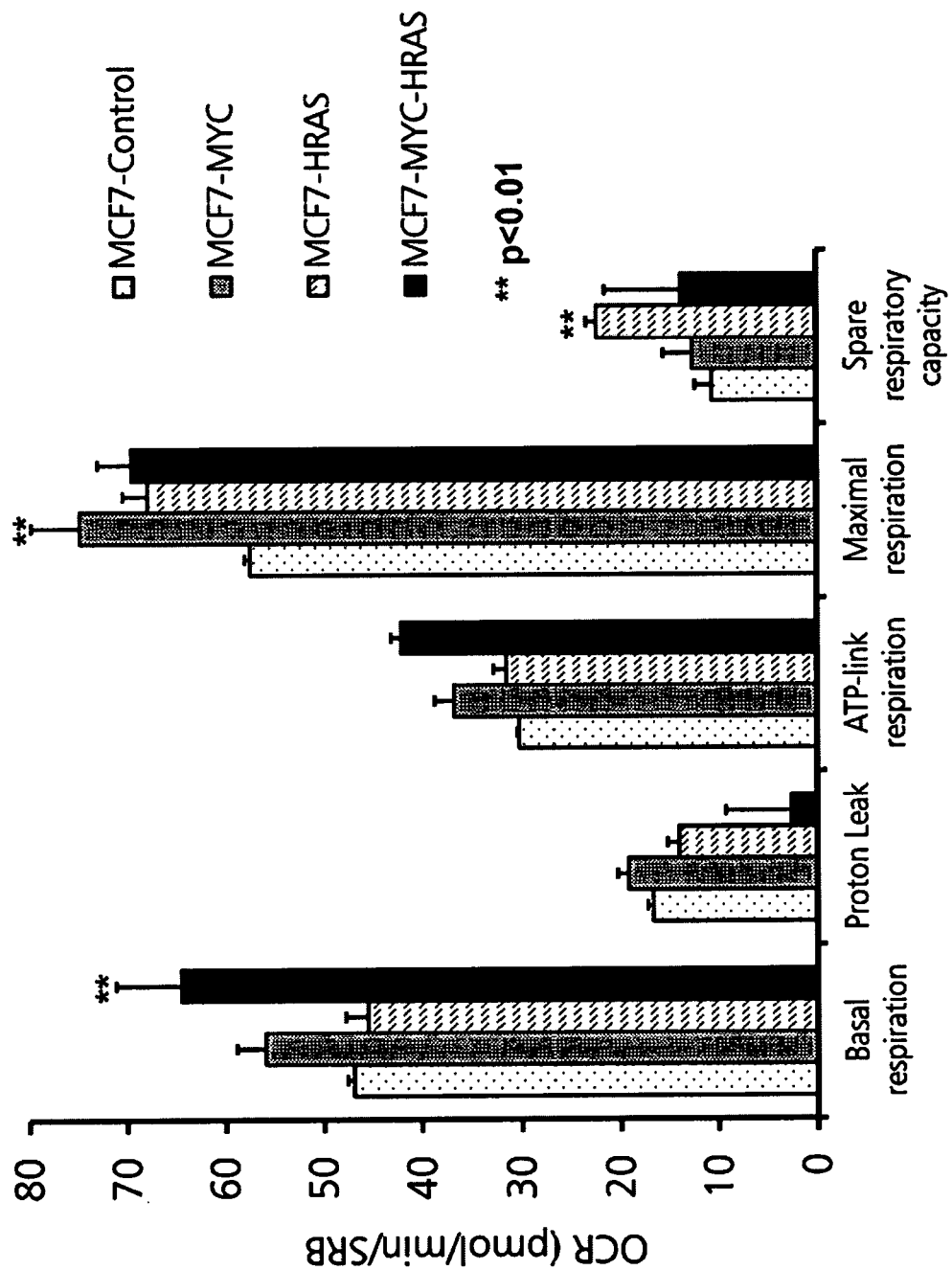
FIG. 2B shows the effects of H-Ras, c-Myc, and H-Ras plus c-Myc on basal respiration, proton leak, ATP-linked respiration, maximal respiration, and spare respiratory capacity.

FIG. 2A shows the effects of H-Ras, c-Myc, and H-Ras plus c-Myc on oxygen consumption rate (OCR). FIG. 2B shows the effects of H-Ras, c-Myc, and H-Ras plus c-Myc on basal respiration, proton leak, ATP-linked respiration, maximal respiration, and spare respiratory capacity. These results show that both c-Myc alone and c-Myc plus H-Ras increase mitochondrial respiration rates.

Figure 3A:
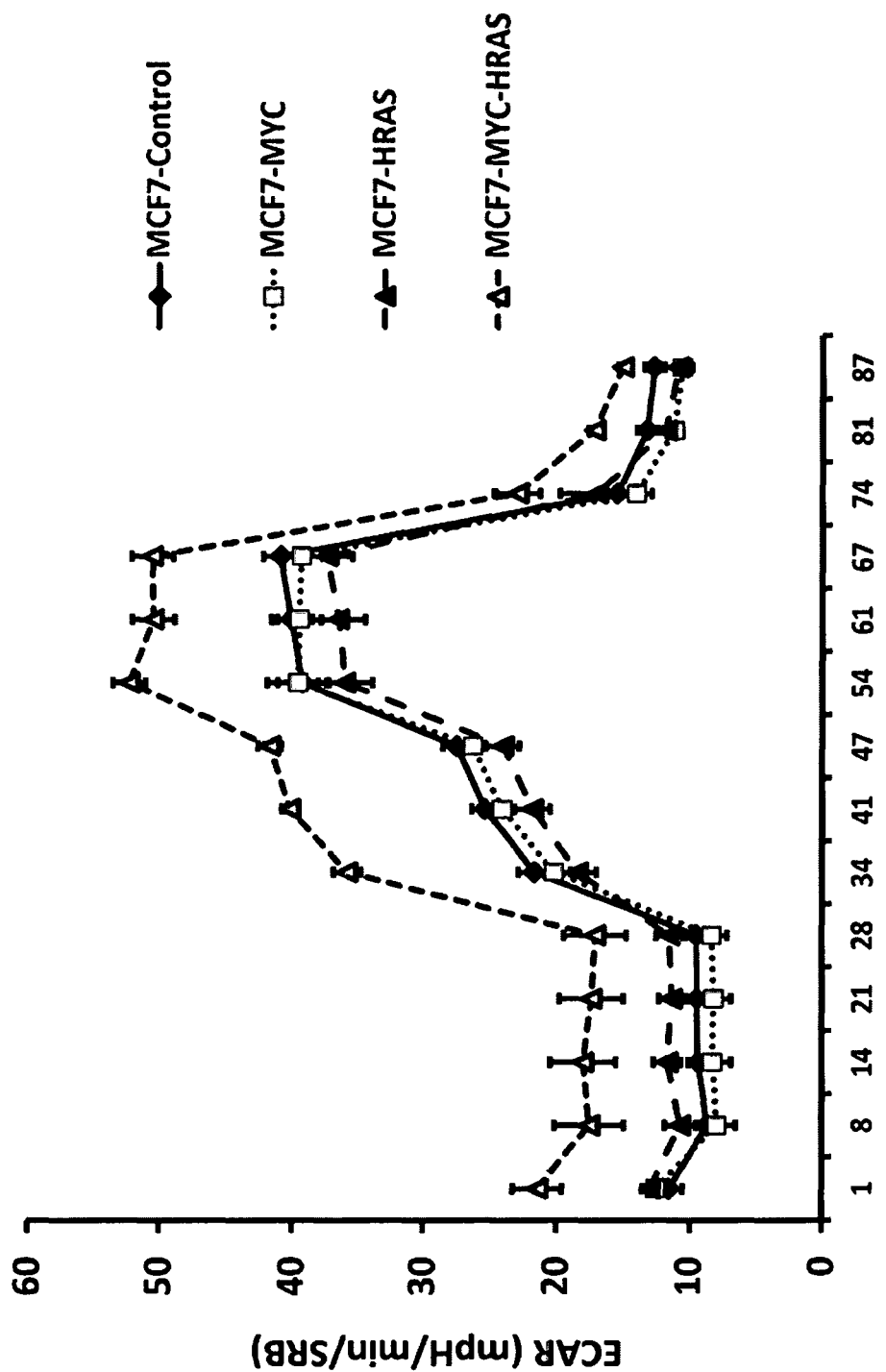
FIG. 3A shows the effects of H-Ras, c-Myc, and H-Ras plus c-Myc on extracellular acidification rate (ECAR).
Figure 3B:
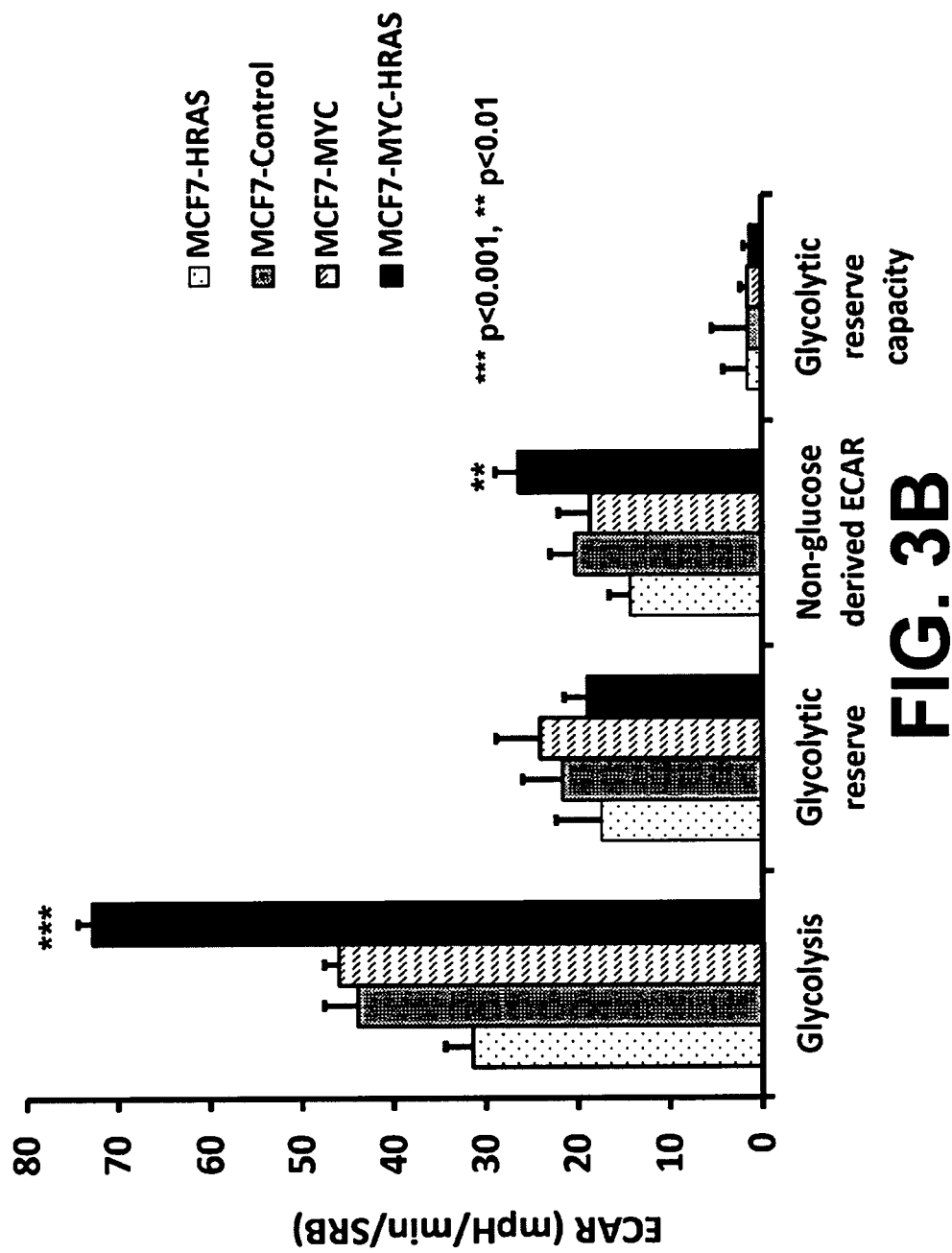
FIG. 3B shows the effects of H-Ras, c-Myc, and H-Ras plus c-Myc on glycolysis, glycolytic reserve, non-glucose derived ECAR, and glycolytic reserve capacity.

FIG. 3A shows the effects of H-Ras, c-Myc, and H-Ras plus c-Myc on extracellular acidification rate (ECAR). FIG. 3B shows the effects of H-Ras, c-Myc, and H-Ras plus c-Myc on glycolysis, glycolytic reserve, non-glucose derived ECAR, and glycolytic reserve capacity. These results show that H-Ras increase glycolysis in cells containing c-Myc overexpression.

Proteomics analysis of MCF7 cells transduced with c-Myc can be conducted to determine the proteins implicated in c-Myc effects on CSCs. MCF7 cells were maintained in DMEM supplemented with 10% FBS (fetal bovine serum), 2 mM GlutaMAX, and 1% Pen-Strep. 8,000 cells per well were seeded into XF96-well cell culture plates, and incubated overnight at 37° C. in a 5% $CO_2$ humidified atmosphere. The next day, cells were washed in pre-warmed XF assay media (for OCR measurement, XF assay media was supplemented with 10 mM glucose 1 mM Pyruvate and adjusted at pH 7.4). Cells were then maintained in 175 μL/well of XF assay media at 37° C., in a non-$CO_2$ incubator for 1 h. During incubation, 25 μL of 80 mM glucose, 9 μM oligomycin, 1M 2-deoxyglucose (for ECAR measurement) and 25 μL of 10 μM oligomycin, 9 μM FCCP, 10 μM rotenone, 10 μM antimycin A (for OCR measurement) in XF assay media was loaded into the injection ports of the XFe-96 sensor cartridge. During the experiment, the instrument injected these inhibitors into the wells at a given time point while ECAR/OCR was measured continuously. ECAR and OCR measurements were normalized by protein content (Sulphorhodamine B assay). Data sets were analyzed by XFe-96 software, using one-way ANOVA and Student's t-test calculations. All experiments were performed in triplicate.

About 26 mitochondrial proteins were elevated in MCF7 cells transduced with c-Myc. These proteins are associated with i) OXPHOS (COX5A, ATP5I, COX5B, UQCR11, and NDUFS1), ii) the TCA cycle (MDH2, IDH3A, PDHB, and SUCLG2), iii) mitochondrial biogenesis (IMMT, TIMM44, TRAP1, HSPD1, SLIRP, TUFM, and TOMM7), or iv) mitochondrial oxidative stress (CHCHD2, PRDX3). These results are summarized in Table 1.

TABLE 1

Proteomics analysis of MCF7 cells transduced with c-Myc.

| Symbol | Gene Description | Fold-Upregulation |
| --- | --- | --- |
| CHCHD2 | Putative coiled-coil-helix-coiled-coil-helix domain-containing protein, mitochondrial | 4.05 |
| PRDX3 | Thioredoxin-dependent peroxide reductase, mitochondrial | 3.96 |
| COX5A | Cytochrome c oxidase subunit 5A, mitochondrial | 3.65 |
| IMMT | Mitochondrial inner membrane protein | 3.54 |
| TRNT1 | CCA tRNA nucleotidyltransferase 1, mitochondrial | 3.22 |
| TIMM44 | Mitochondrial import inner membrane translocase subunit TIM44 | 3.15 |
| C21orf33 | ES1 protein homolog, mitochondrial (HES1) | 3 |
| AKAP1 | A kinase anchor protein 1, mitochondrial | 2.72 |
| MDH2 | Malate dehydrogenase, mitochondrial (EC 1.1.1.37) | 2.69 |
| IDH3A | Isocitrate dehydrogenase [NAD] subunit alpha, mitochondrial | 2.64 |
| TRAP1 | Heat shock protein 75 kDa, mitochondrial | 2.4 |
| FASN | Fatty acid synthase | 2.16 |
| HADHB | Trifunctional enzyme subunit beta, mitochondrial | 2.13 |
| CLUH | Clustered mitochondria protein homolog/KIAA0664 | 2.12 |
| ATP5I | ATP synthase subunit e, mitochondrial | 1.98 |
| ABAT | 4-aminobutyrate aminotransferase, mitochondrial | 1.97 |
| CLPX | ATP-dependent Clp protease ATP-binding subunit clpX-like, mitochondrial | 1.94 |
| HSPD1 | 60 kDa heat shock protein, mitochondrial | 1.89 |
| SLIRP | SRA stem-loop-interacting RNA-binding protein, mitochondrial | 1.81 |
| TUFM | Elongation factor Tu, mitochondrial | 1.75 |
| COX5B | Cytochrome c oxidase subunit 5B, mitochondrial | 1.69 |
| PDHB | Pyruvate dehydrogenase E1 component subunit beta, mitochondrial | 1.64 |
| UQCR11 | Cytochrome b-c1 complex subunit | 1.64 |
| SUCLG2 | Succinyl-CoA ligase [GDP-forming] subunit beta, mitochondrial | 1.6 |
| NDUFS1 | Mitochondrial NADH-ubiquinone oxidoreductase 75 kDa subunit | 1.51 |
| TOMM7 | Mitochondrial import receptor subunit TOM7 homolog | 1.49 |

Figure 4:
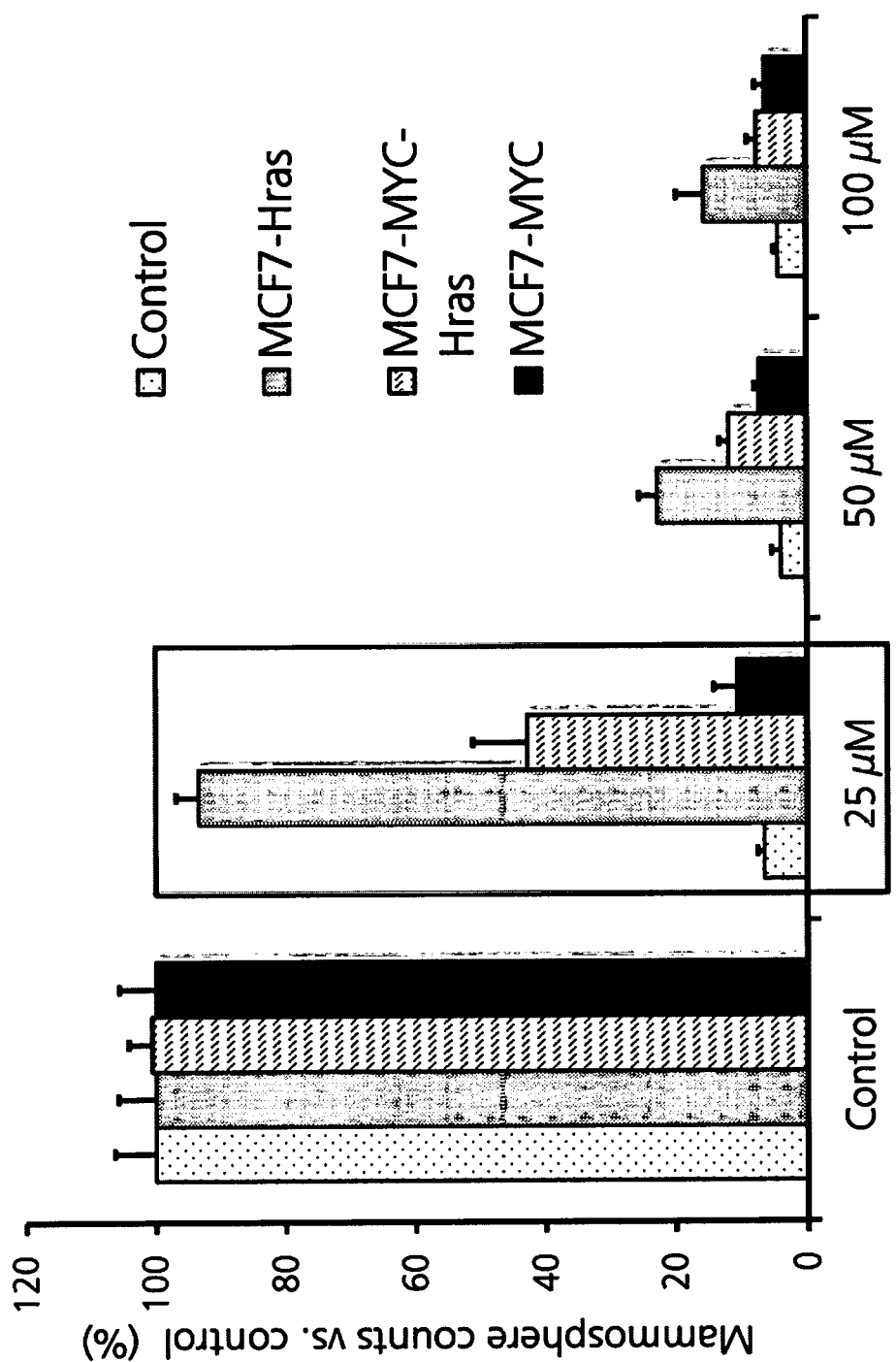
FIG. 4 shows the effects of doxycycline treatment on H-Ras, c-Myc, and H-Ras plus c-Myc induced mammosphere formation.

The inventors hypothesized that mitochondrial inhibitors may target c-Myc amplification in CSCs. To test this hypothesis, inventors tested the effects of doxycycline, an antibiotic that inhibits mitochondrial biogenesis as an off-target effect. It should be appreciated that the present approach may be used with other mitochondrial biogenesis inhibitors. This includes, for example, mitoriboscins as described in U.S. Provisional Patent Application 62/471,688 filed Mar. 15, 2017 and incorporated herein by reference in its entirety; antimitoscins as described in U.S. Provisional Patent Application 62/508,702 filed May 19, 2017 and incorporated herein by reference in its entirety; and mitoketoscins as described in U.S. Provisional Patent Application 62/524,829 filed Jun. 26, 2017 and incorporated herein by reference in its entirety. FIG. 4 shows that c-Myc-H-Ras-induced mammosphere formation is sensitive to doxycycline treatment.

Figure 5A:
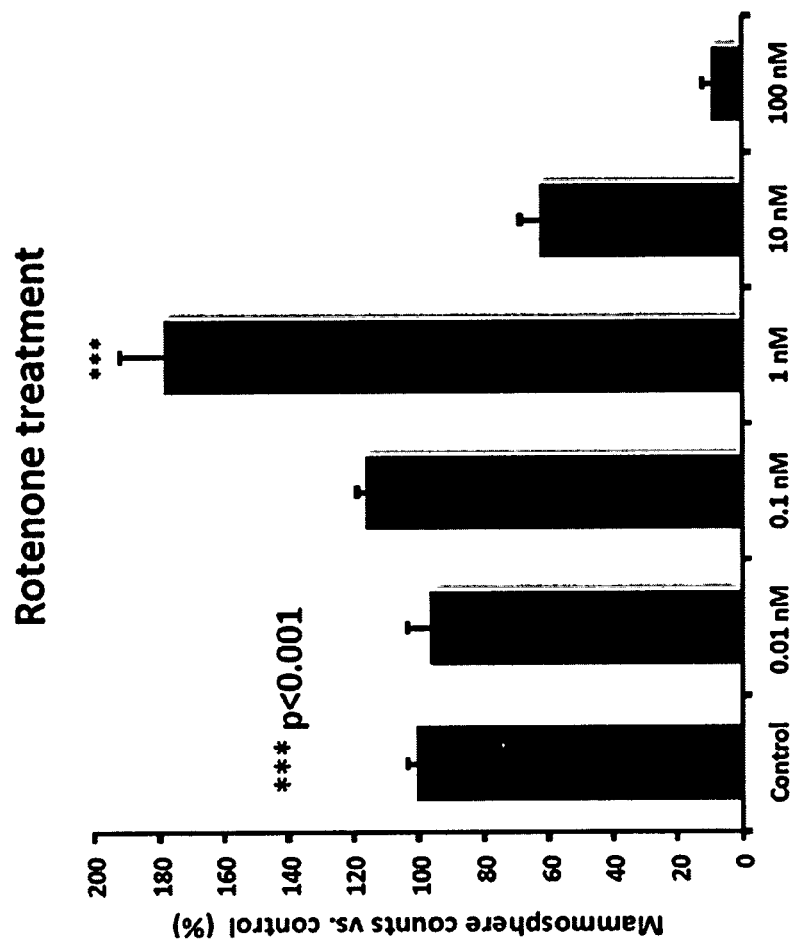
FIG. 5A shows the effects of higher dose rotenone treatment on mammosphere formation in MCF7 cells.
Figure 5B:
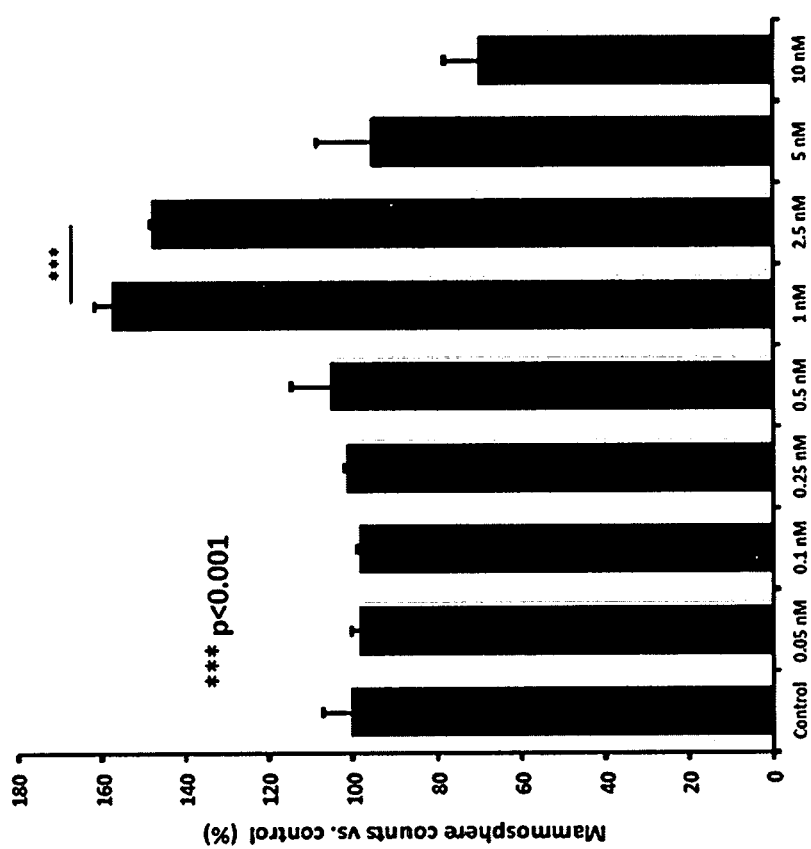
FIG. 5B shows the effects of lower dose rotenone treatment on mammosphere formation in MCF7 cells.

The inventors hypothesized that c-Myc induces "stemness" of CSCs in part by driving and managing the onset of mitochondrial oxidative stress. To test this hypothesis, inventors used a pharmacological approach to stimulate oxidative stress. Rotenone is a naturally occurring isoflavone that behaves as an inhibitor of complex I and strongly induces mitochondrial oxidative stress. During rotenone treatment, mitochondrial complexes I and III are the major sites of electron leakage, resulting in increased superoxide production. The inventors treated MCF7 cells with increasing concentrations of Rotenone. FIG. 5 shows that low-dose Rotenone stimulated mammosphere formation by about 1.6 to 1.8-fold. In contrast, higher dose Rotenone inhibited mammosphere formation due to lethal/toxic levels of oxidative stress.

Figure 6A:
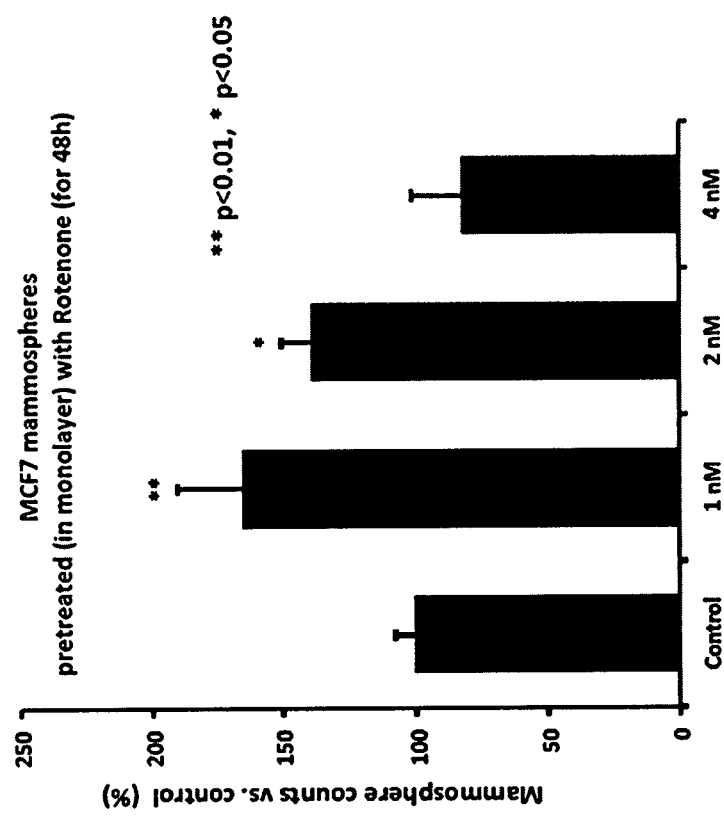
FIG. 6A shows the effects of Mito-tempo treatment on MCF7 mammospheres pretreated with rotenone.
Figure 6B:
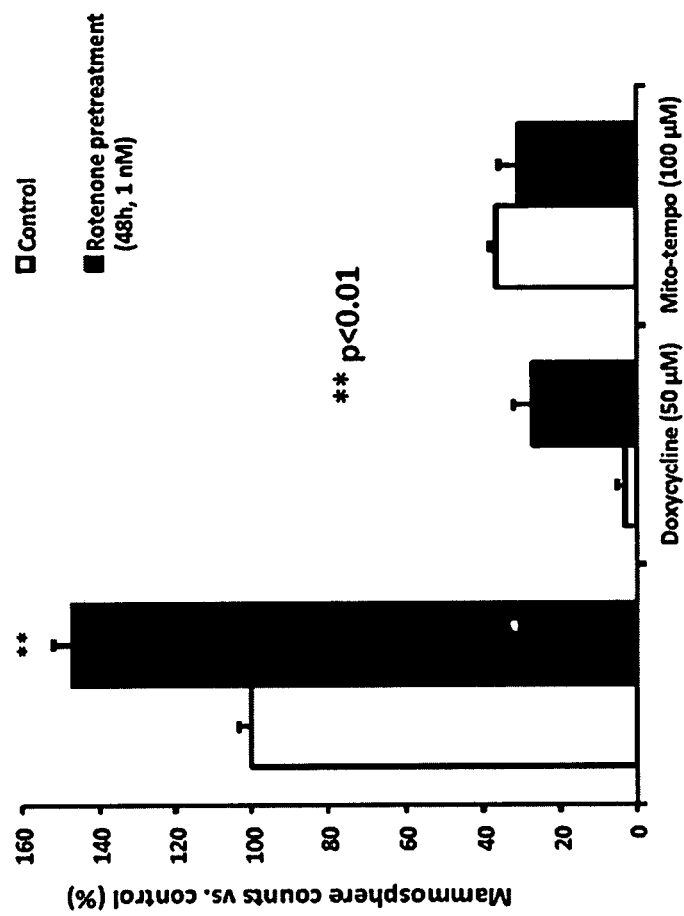
FIG. 6B shows the effects of Mito-tempo and doxycycline treatment on MCF7 mammospheres pretreated with rotenone.

To further validate that the effects of low-dose Rotenone were due to oxidative stress, the inventors tested the effects of a mitochondrial-specific antioxidant Mito-tempo. Mito-tempo functions as a reactive oxygen species (ROS) scavenger by targeting superoxide anions generated in mitochondria. FIG. 6 demonstrates Mito-tempo treatment inhibited the stimulatory effects of rotenone on mammosphere formation in MCF7 cells. Identical effects were observed with doxycycline treatment, which functions as a known inhibitor of mitochondrial biogenesis.

Generally, c-Myc and H-Ras, as well as mitochondrial oxidative stress, lead to increases in mitochondrial biogenesis. which in turn furthers CSC propagation. As discussed herein, certain anti-mitochondrial inhibitors therapeutically block the effect of H-Ras, c-Myc, and Rotenone on CSC propagation. Doxycycline, for example, is capable of inhibiting this propagation. Mitoriboscins, mitoketoscins, and antimitoscins (descriptions of which have been incorporated by reference above) also inhibit CSC propagation.

To determine the potential clinical relevance of the findings, the inventors assessed whether the c-Myc mitochondrial targets identified in MCF7 cells were transcriptionally upregulated in human breast cancer cells in vivo. Inventors considered a published clinical data set of breast cancer patients in which their tumor samples were captured via laser-capture micro-dissection. To perform Kaplan-Meier (K-M) analysis of nuclear mitochondrial gene transcripts, inventors used an open-access online survival analysis tool to interrogate publicly available microarray data from up to 3,951 breast cancer patients. Inventors primarily analyzed data from ER-positive patients that were lymph node (LN)-positive at diagnosis, luminal A sub-type, and that were primarily treated with tamoxifen and not other chemotherapies (N=152 patients). In this group, 100% the patients received some form of hormonal therapy and >90% of them received tamoxifen. Biased and outlier array data were excluded from the analysis. Hazard-ratios were calculated, at the best auto-selected cut-off, and p-values were calculated using the log-rank test and plotted in R. K-M curves were also generated online using the K-M-plotter (as high-resolution TIFF files), using univariate analysis.

Overall, nearly 80% of the c-Myc mitochondrial targets identified in MCF7 cells in vitro were also transcriptionally elevated in human breast cancer cells in vivo. Table 2 below summarizes these findings. Transcriptional profiling data derived from the analysis of 28 breast cancer patients are shown, high-lighting the levels of fold-upregulation observed in the epithelial cancer cell compartment (relative to the tumor stroma), and corresponding p-values derived from the analysis of these clinical samples. This observation provided a strong indication that the mitochondrial Myc targets identified in both experiments are of high clinical relevance.

TABLE 2

Myc-targets transcriptionally upregulated in human breast in vivo (cancer epithelia vs. tumor stroma)

| Symbol | Gene Description | Fold-Upregulation | P-value |
|---|---|---|---|
| CHCHD2 | Putative coiled-coil-helix domain-containing protein, mitochondrial | 5.79 | 1.85E−07 |
| COX5B | Cytochrome c oxidase subunit 5B, mitochondrial | 5.03 | 2.86E−06 |
| PRDX3 | Thioredoxin-dependent peroxide reductase, mitochondrial | 4.99 | 3.30E−06 |
| IMMT | Mitochondrial inner membrane protein | 4.71 | 8.89E−06 |
| PDHB | Pyruvate dehydrogenase E1 component subunit beta, mitochondrial | 4.51 | 1.75E−05 |
| MDH2 | Malate dehydrogenase, mitochondrial (EC 1.1.1.37) | 4.18 | 5.32E−05 |
| COX5A | Cytochrome c oxidase subunit 5A, mitochondrial | 3.62 | 3.22E−04 |
| C21orf33 | ES1 protein homolog, mitochondrial (HES1) | 3.6 | 3.49E−04 |
| UQCR11 | Cytochrome b-c1 complex subunit (UQCR) | 3.43 | 5.87E−04 |
| HSPD1 | 60 kDa heat shock protein, mitochondrial | 3.42 | 5.93E−04 |
| TUFM | Elongation factor Tu, mitochondrial | 3.38 | 6.74E−04 |
| AKAP1 | A kinase anchor protein 1, mitochondrial | 3.33 | 7.75E−04 |
| NDUFS1 | Mitochondrial NADH-ubiquinone oxidoreductase 75 kDa subunit | 3.2 | 1.15E−03 |
| HADHB | Trifunctional enzyme subunit beta, mitochondrial | 3.06 | 1.73E−03 |
| SUCLG2 | Succinyl-CoA ligase [GDP-forming] subunit beta, mitochondrial | 3.03 | 1.89E−03 |
| TOMM7 | Mitochondrial import receptor subunit TOM7 homolog | 3.03 | 1.85E−03 |
| ATP5I | ATP synthase subunit e, mitochondrial | 3.01 | 1.97E−03 |
| IDH3A | Isocitrate dehydrogenase [NAD] subunit alpha, mitochondrial | 2.16 | 1.78E−02 |
| CLPX | ATP-dependent Clp protease ATP-binding subunit clpX-like, mitochondrial | 2.11 | 1.96E−02 |
| ABAT | 4-aminobutyrate aminotransferase, mitochondrial | 2.08 | 2.14E−02 |

Figure 7:
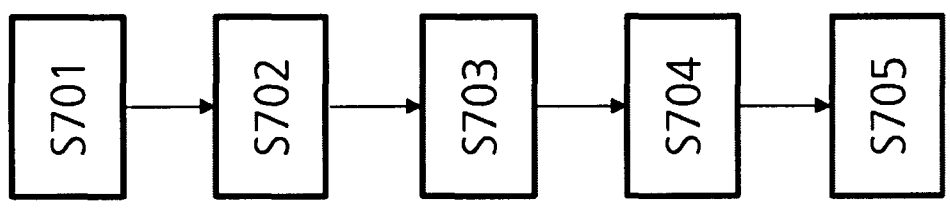
FIG. 7 outlines a general approach to Myc-driven breast cancer biomarker development.

Inventors next assessed the prognostic significance of the c-Myc-induced mitochondrial targets identified by proteomics analysis. FIG. 7 provides a work-flow diagram illustrating the informatics-based approach to oncogene-driven breast cancer biomarker development. First, proteomics analysis of MCF7 cells harboring c-Myc is performed (S701). The investigator then focuses on the nuclear mitochondrial genes related to mitochondrial biogenesis and OXPHOS (S702). Next, the investigator determines whether mitochondrial-associated protein transcripts have prognostic value through bioinformatics analysis (S703). As an example, breast cancer would involve ER+, Luminal A, LN+, Tamoxifen-treated, and >15-years follow-up. Then short prognostic signatures may be generated (e.g., the intersection of new proteomics data, with transcriptional gene profiling and outcome data) (S704). New targets and predictors of treatment failure and/or drug resistance (tumor recurrence, distant metastasis, and/or companion diagnostics) may be identified (S705). Inventors used publicly available transcriptional profiling data from the tumors of breast cancer patients that were treated with tamoxifen but not any chemotherapy. Inventors selected high-risk patients that were lymph-node positive at diagnosis and focused on luminal A subtype, which represents the most common form of ER-positive breast cancers. Using this approach, the inventors identified 5 gene transcripts and 9 gene probes that showed high prognostic value, as is shown in Table 3 below.

TABLE 3

Prognostic value of individual c-Myc targets in human breast cancer patients (ER-positive, luminal A, LN-positive, treated with anti-estrogen (mostly Tamoxifen); Relapse-free survival (RFS); N = 152).

| Symbol | Gene Probe | HR (Hazzard Ratio) | P-value (Log Rank Test) |
|---|---|---|---|
| HSPD1 | 200807_s_at | 3.46 | 1.30e−05 |
| HSPD1 | 200806_s_at | 2.34 | 0.0049 |
| TIMM44 | 203093_s_at | 2.51 | 0.0042 |
| COX5B | 213735_s_at | 2.51 | 0.0012 |
| COX5B | 202343_x_at | 2.3 | 0.0032 |
| COX5B | 211025_x_at | 2.13 | 0.0077 |
| IDH3A | 202069_s_at | 2.46 | 0.0026 |
| IDH3A | 202070_s_at | 2.25 | 0.0089 |
| TRAP1 | 221235_s_at | 1.77 | 0.048 |

To increase the prognostic power of the mitochondrial biomarkers, the inventors selected the biomarkers with high hazard ratio values and used them to create a c-Myc-based Mito-Signature that contains three genes—HSPD1, COX5B, and TIMM44. This Mito-Signature combines: i) a mitochondrial chaperone (HSPD1) with ii) an OXPHOS subunit (COX5B, from Complex IV) and iii) a marker of mitochondrial biogenesis (TIMM44 or Translocase of Inner Mitochondrial Membrane 44). These results are summarized in Tables 4 and 5 shown below.

TABLE 4

Prognostic value of a c-Myc-based Mito-Signature in human breast cancer patients (tumor recurrence) (ER-positive, luminal A, LN-positive, treated with anti-estrogen (mostly Tamoxifen); Relapse-free survival (RFS); N = 152).

| Symbol | Gene Probe | HR (Hazzard Ratio) | P-value (Log Rank Test) |
|---|---|---|---|
| HSPD1 | 200807_s_at | 3.46 | 1.30e−05 |
| COX5B | 213735_s_at | 2.51 | 0.0012 |
| TIMM44 | 203093_s_at | 2.51 | 0.0042 |
| Combined | | 4.69 | 2.4e−08 |

TABLE 5

Prognostic value of a c-Myc-based Mito-Signature in human breast cancer patients (distant metastasis) (ER-positive, luminal A, LN-positive, treated with anti-estrogen (mostly Tamoxifen); Distant Metastasis Free Survival (DMFS); N = 149).

| Symbol | Gene Probe | HR (Hazzard Ratio) | P-value (Log Rank Test) |
|---|---|---|---|
| HSPD1 | 200807_s_at | 3.5 | 9.7e−05 |
| COX5B | 213735_s_at | 3.2 | 0.00075 |
| TIMM44 | 203093_s_at | 3.06 | 0.0024 |
| Combined | | 4.94 | 2.8e−07 |

Figure 8A:
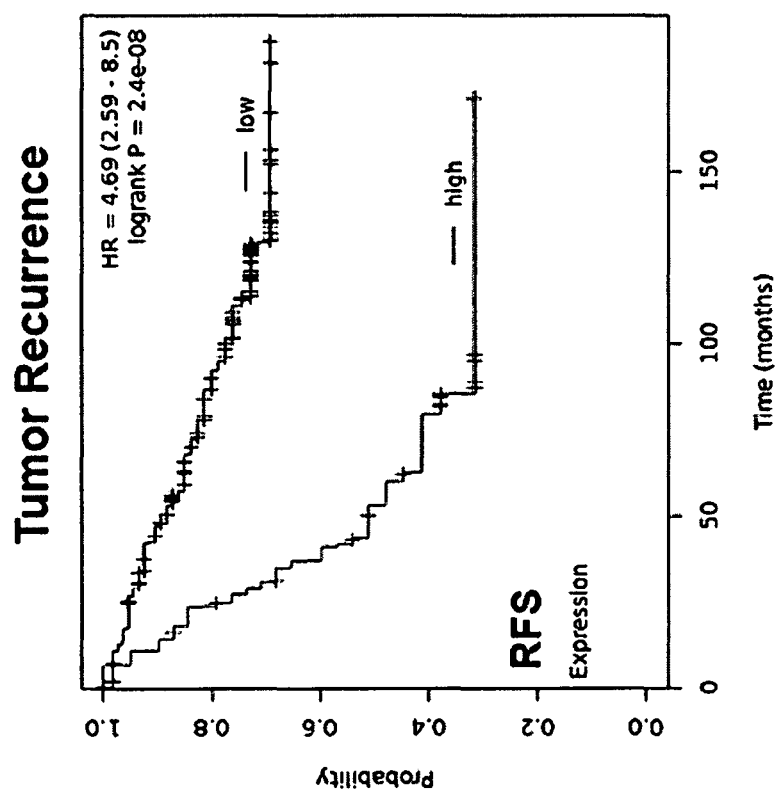
FIG. 8A shows relapse-free survival rates for tumor reoccurrence using the Myc-based Mito-Signature.
Figure 8B:
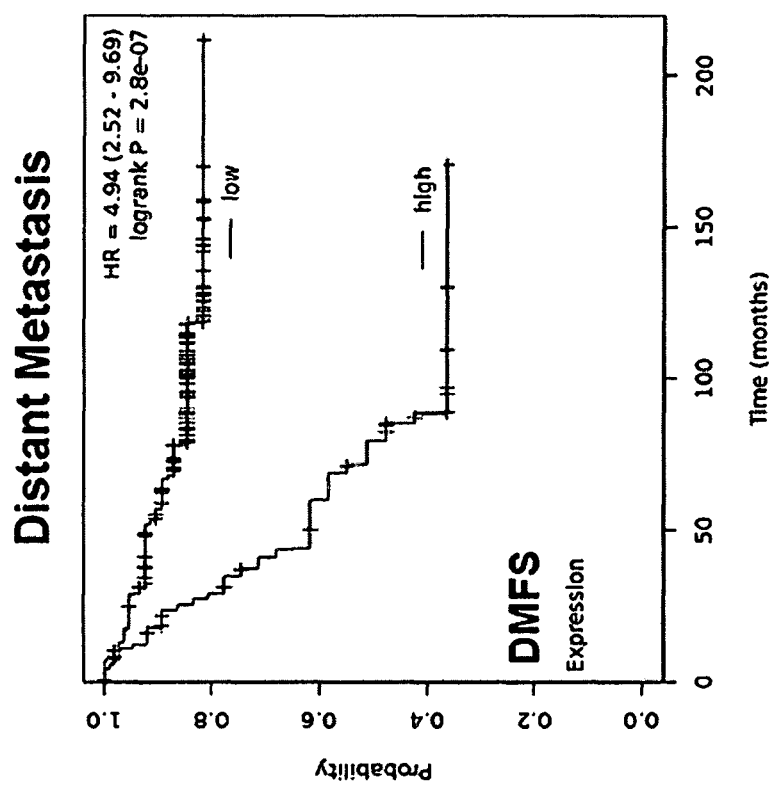
FIG. 8B shows metastasis-free survival rates for the Myc-based Mito-signatures.

FIG. 8A shows the results of the K-M analysis for relapse-free survival (RFS) for the Myc-based Mito-Signature. Similar results were obtained for distant metastasis-free survival, as shown in FIG. 8B. Therefore, this Myc-based Mito-Signature may be effective at predicting tamoxifen resistance and treatment failure for endocrine therapy.

Figure 9A:
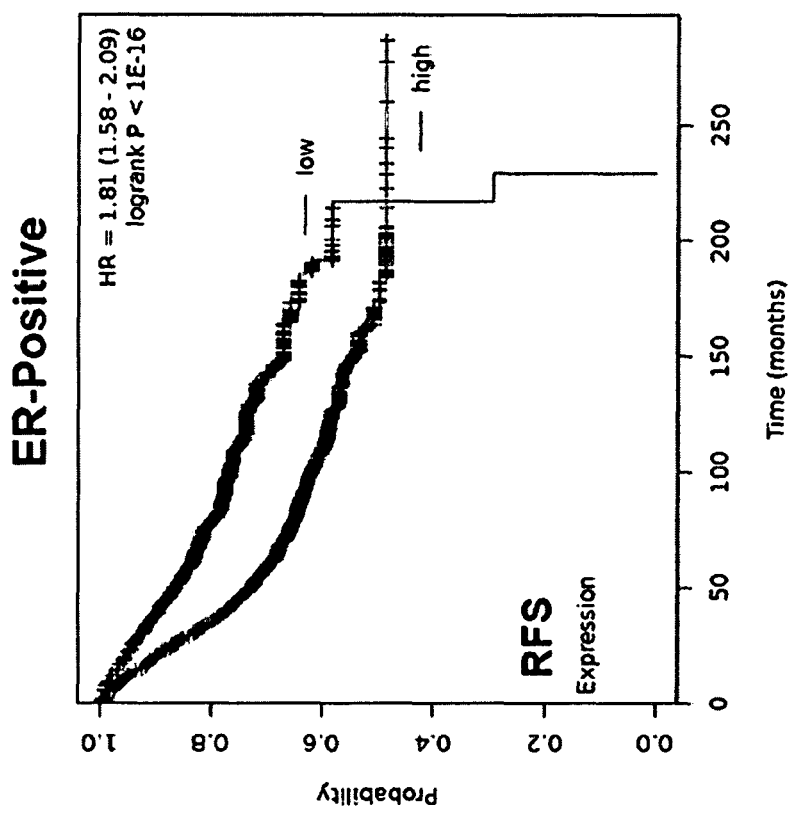
FIG. 9A shows relapse-free survival rates for estrogen receptor (ER)-positive cancers using the Myc-based Mito-signature.
Figure 9B:
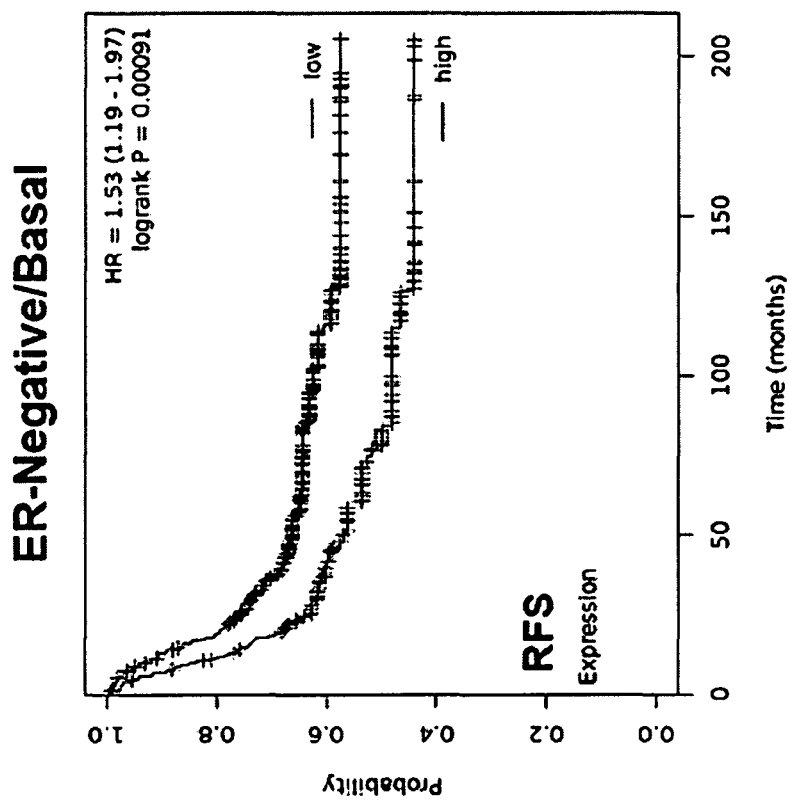
FIG. 9B shows relapse-free survival rate for ER-negative/basal cancers using the Myc-based Mito-signature.
Figure 9C:
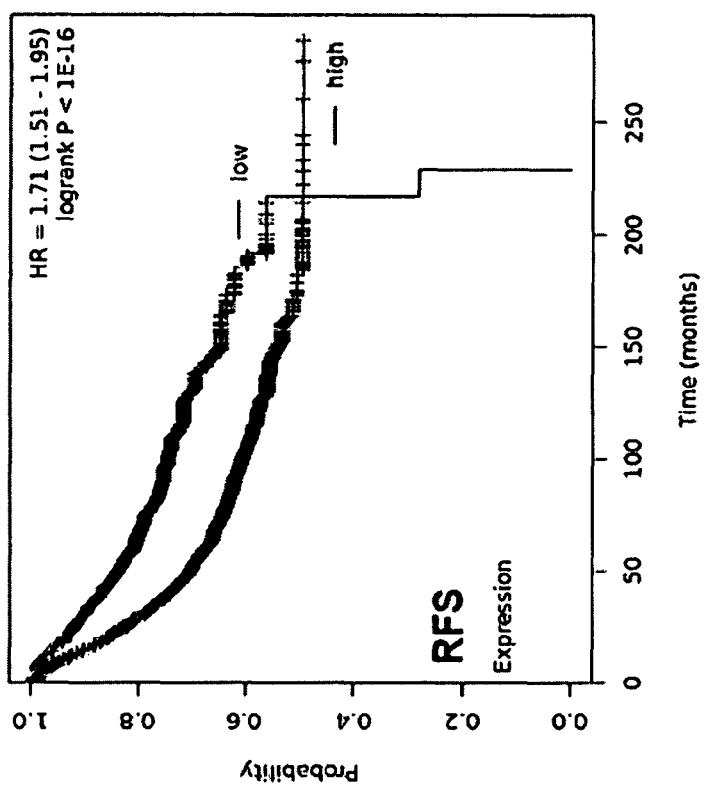
FIG. 9C shows relapse-free survival rates for all breast cancer subtypes using the Myc-based Mito-signature.

The inventors also assessed the behavior of the Myc-based Mito-Signature in a larger patient population where the therapy was not restricted to tamoxifen. FIG. 9A-C shows that the Myc Mito-Signature effectively predicted poor clinical outcome (relapse-free survival (RFS)) in ER-positive (FIG. 9A) and ER-negative (FIG. 9B) breast cancer populations and all breast cancer subtypes combined (FIG. 9C). The Myc-based Mito-signature therefore may represent an important prognostic tool for predicting patient outcomes in a wide variety of breast cancer patient populations.

Figure 10:
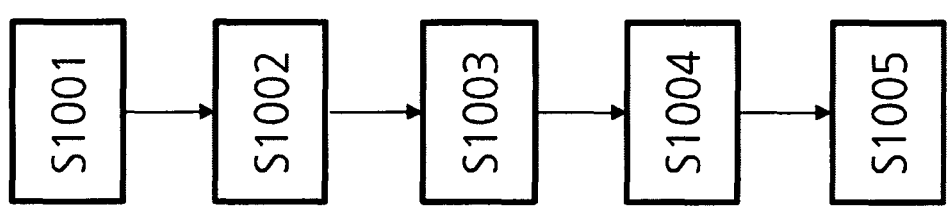
FIG. 10 outlines steps for the development of companion diagnostics.

Based on the inventors' findings, inventors developed a strategy for development of companion diagnostics that is outlined in FIG. 10. First, a cell line harboring a genetic, epigenetic, or metabolic change may be generated (S1001). For example, an oncogene may be activated or a tumor suppressor gene may be inactivated. Second, a global unbiased proteomics analysis may be performed. In some embodiments, metabolic genes (e.g., mitochondrial, glycolysis, fatty acid oxidation, pentose phosphate pathway) may be the focus of analysis (S1002). Next, bioinformatics analysis may be used to determine whether metabolism-associated protein transcripts have prognostic value (S1003). This may be done for any cancer type, and may involve patient follow-up data. Next, short prognostic signatures may be generated (S1004). These may intersect new proteomics data with transcriptional gene profiling data and outcome data. It should be appreciated that transcriptional gene profiling data and outcome data may be pre-existing and often is publicly available. Finally, new targets and predictors of treatment failure and/or drug resistance may be identified (S1005).

This simplified strategy may be potentially applied to any cancer type. As described above, generally the first step involves the generation of a novel cellular model, which is interrogated by proteomics analysis. Then, these results are used to establish the prognostic value of these candidate biomarkers, by searching pre-existing human transcriptional profiling data linked to clinical outcome (in silico validation). The prognostic value of these biomarkers may also be enhanced significantly by using more than one marker in combination, thereby forming a short signature.

Figure 11:
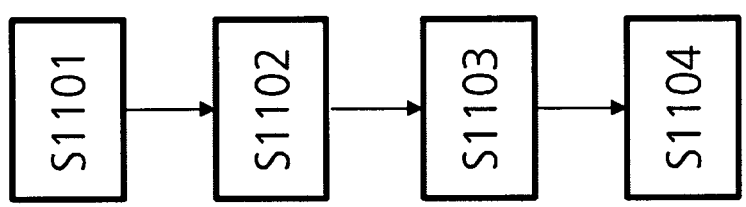
FIG. 11 outlines steps of a proteomics-to-genomic approach to in silico validation of biomarkers.
Figure 12:
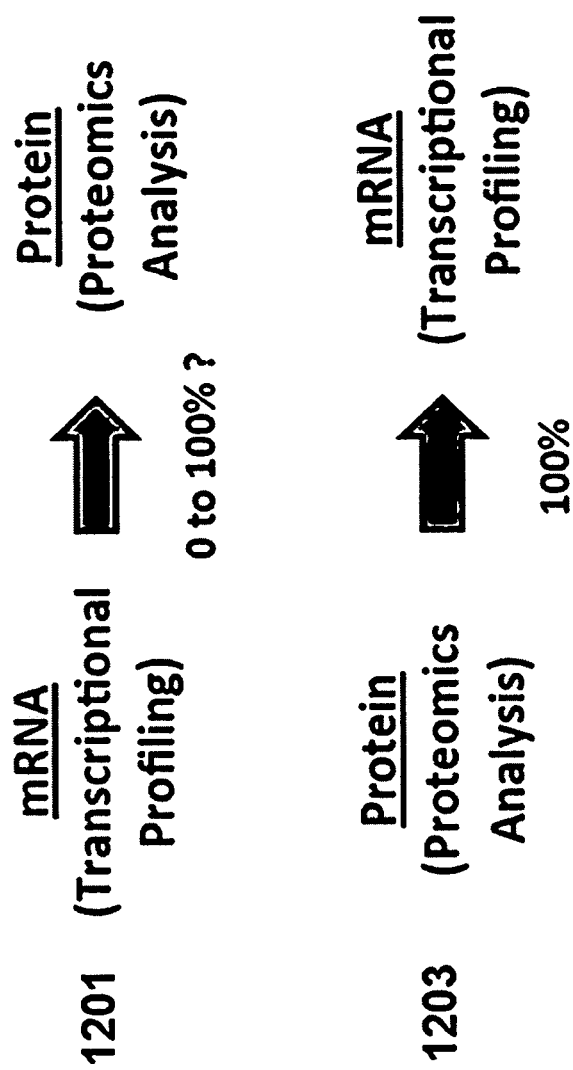
FIG. 12 illustrates how analysis using proteomics data first and integrating it with existing transcriptional profiling data allows for more effective biomarker development.

This "Proteomics-to-Genomics (PTG)" approach efficiently yields new targets and biomarkers, linked to parameters associated with clinical outcome (tumor recurrence, distant metastasis, overall survival, or response to therapy). FIG. 11 outlines the steps of a proteomics-to-genomics approach to in silico validation. Proteomics data from a cellular model is directly used (S1101) to interrogate existing genomics data (transcriptional profiling) from clinical samples (S1102), which may be linked to follow-up data (S1103). This approach directly allows for the in silico validation of i) the prognostic value (of a given candidate biomarker) and ii) helps to generate new targets for drug development, by directly demonstrating their clinical relevance (S1104). Using the PTG approach, an experimental strategy for understanding MYC and RAS cooperativity in human breast CSCs is disclosed herein. This strategy first accepts that c-Myc and H-Ras (G12V) cooperation affects cellular metabolism and CSC propagation. This co-operativity, in turn, allows for the identification of a common metabolic therapy. FIG. 12 shows the advantages of the PTG approach 1203 over traditional approaches 1201 to biomarker development. FIG. 12 illustrates how, in traditional approach 1201, mRNA levels may not necessarily correlate with protein levels, creating a bottle-neck for protein biomarker development. The concordance between mRNA and protein may be quite variable and unpredictable, ranging anywhere between 0 and 100%. This discordance between mRNA and protein expression levels ultimately makes it difficult or impossible to use transcriptional profiling data for the development of new protein biomarkers as companion diagnostics. In contrast, the PTG strategy 1203 described herein provides a simple straightforward solution to this practical problem. By starting out with proteomics data first and then integrating it with existing transcriptional profiling data, one may quickly identify and select a sub-set of genes, with tight correlations, nearing 100%. It essentially allows one to "work-backwards", providing a much needed systematic "short-cut" to protein biomarker development.

The present approach has a wide range of applications. For example, anti-mitochondrial antibodies directed against biomarkers or Mito-Signatures identified under the present approach may be used to immuno-stain tumor tissue sections. Such embodiments may be used to assess or predict clinical outcome. The HSPD1, COX5B, and/or TIMM44 biomarkers and Mito-Signature discussed in the specific embodiments above are demonstrative. As another example, fluorescent-antibodies directed against biomarkers or Mito-Signatures identified under the present approach (including, e.g., the HSPD1, COX5B, and/or TIMM44 biomarkers and Mito-Signatures described above) may be used to detect and/or isolate CSCs from tumor tissue. Such embodiments may employ fluorescence-activated cell sorting (FACS) and flow cytometry techniques as are known in the art. Such fluorescent-antibodies may also be used to detect and/or isolate circulating tumor cells (CTCs) from blood, through, as an example, FACS and flow cytometry. In yet another example, antibodies directed against biomarkers or Mito-Signatures identified under the present approach may be coupled to magnetic beads or other magnetic elements. Magnetized antibodies may then be used to detect and/or isolate CSCs and CTCs. It should be appreciated that these examples are merely representative of the applicability of the present approach, and should not be construed as limiting the present approach.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method of detecting cancer stem cells in a tissue sample, the method comprising:
    preparing a plurality of fluorescent antibodies containing an antibody directed against each Myc-based biomarker in a gene signature of HSPD1, COX5B, and TIMM44;
    administering the prepared plurality of fluorescent antibodies to the sample;
    sorting cells from the sample based on fluorescence; and
    detecting cancer stem cells based on the sorted cells.

2. The method of claim 1, wherein the Myc-based biomarker consists of HSPD1, COX5B, and TIMM44.

3. A method of isolating cancer stem cells in a tissue sample, the method comprising:
    preparing a plurality of fluorescent antibodies containing an antibody directed against each Myc-based biomarker in a gene signature of HSPD1, COX5B, and TIMM44;
    administering the prepared plurality of fluorescent antibodies to the sample;
    sorting cells from the sample based on fluorescence, and
    separating cells based on the presence of the fluorescent antibody.

4. The method of claim 3, wherein the Myc-based biomarker consists of HSPD1, COX5B, and TIMM44.

5. A method of detecting cancer stem cells in a tissue sample, the method comprising:
    preparing a plurality of antibodies containing an antibody directed against each Myc-based biomarker in a gene signature of HSPD1, COX5B, and TIMM44;
    coupling each prepared antibody with a magnetic element,
    administering the coupled antibodies to the sample,
    sorting magnetic cells from the sample, and
    detecting the presence of the magnetic element in the sorted cells.

6. The method of claim 5, wherein the Myc-based biomarker consists of HSPD1, COX5B, and TIMM44.

7. The method of claim 5, wherein the magnetic element comprises magnetic beads.

8. A method of isolating cancer stem cells in a tissue sample, the method comprises:
    preparing a plurality of antibodies containing an antibody directed against each Myc-based biomarker in a gene signature of HSPD1, COX5B, and TIMM44;
    coupling each prepared antibody with a magnetic element,
    administering the coupled antibodies to the sample,
    sorting magnetic cells from the sample, and detecting the presence of the magnetic element in the sorted cells.

9. The method of claim 8, wherein the Myc-based biomarker consists of HSPD1, COX5B, and TIMM44.

10. The method of claim 8, wherein the magnetic element comprises magnetic beads.

* * * * *